(12) United States Patent
Trollsas et al.

(10) Patent No.: US 9,504,772 B2
(45) Date of Patent: Nov. 29, 2016

(54) POLYMERS COMPRISING AMORPHOUS TERPOLYMERS AND SEMICRYSTALLINE BLOCKS

(71) Applicant: Abbott Cardiovascular Systems Inc., Santa Clara, CA (US)

(72) Inventors: Mikael Trollsas, San Jose, CA (US); Michael Ngo, San Jose, CA (US); Florencia Lim, Union City, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 14/203,339

(22) Filed: Mar. 10, 2014

(65) Prior Publication Data
US 2014/0193475 A1   Jul. 10, 2014

Related U.S. Application Data

(62) Division of application No. 12/466,302, filed on May 14, 2009, now Pat. No. 8,697,110.

(51) Int. Cl.
| | |
|---|---|
| *A61L 31/04* | (2006.01) |
| *A61L 31/06* | (2006.01) |
| *A61L 31/10* | (2006.01) |
| *A61L 31/16* | (2006.01) |
| *C08L 67/04* | (2006.01) |
| *C08L 77/12* | (2006.01) |

(52) U.S. Cl.
CPC ............. *A61L 31/041* (2013.01); *A61L 31/06* (2013.01); *A61L 31/10* (2013.01); *A61L 31/16* (2013.01); *C08L 67/04* (2013.01); *C08L 77/12* (2013.01)

(58) Field of Classification Search
None
See application file for complete search history.

(56) References Cited

U.S. PATENT DOCUMENTS

| | | | |
|---|---|---|---|
| 5,085,629 A * | 2/1992 | Goldberg et al. | 604/8 |
| 2005/0281856 A1* | 12/2005 | McGlohorn et al. | 424/423 |
| 2008/0014238 A1* | 1/2008 | Trollsas | A61L 27/18 424/422 |
| 2009/0111787 A1* | 4/2009 | Lim et al. | 514/178 |

* cited by examiner

Primary Examiner — Brian Gulledge
(74) Attorney, Agent, or Firm — Squire Patton Boggs (US) LLP

(57) ABSTRACT

The present invention provides an implantable article comprising an amorphous terpolymer and a semi-crystalline polymer. The amorphous terpolymer can be admixed with the semi-crystalline polymer or form a block copolymer with the semi-crystalline polymer.

18 Claims, No Drawings

POLYMERS COMPRISING AMORPHOUS TERPOLYMERS AND SEMICRYSTALLINE BLOCKS

CROSS-REFERENCE TO RELATED APPLICATION

This application is a divisional application of U.S. application Ser. No. 12/466,302 filed on May 14, 2009, the teaching of which is incorporated herein by reference in its entirety.

FIELD OF THE INVENTION

The present invention relates to a semi-crystalline composition for coating an implantable device.

BACKGROUND OF THE INVENTION

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of the arterial lining and to reduce the chance of thrombosis or restenosis, a stent is implanted in the artery to keep the artery open.

Drug delivery stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, a few challenges remain in the art of drug delivery stents. For example, compromised coating integrity when an amorphous bioabsorbable polymer is used for coating a stent, which can result from the conditions of ethylene oxide (ETO) sterilization or from the conditions of crimping a stent onto the delivery balloon. Conditions such as elevated temperature, high relative humidity, and high concentration of ETO in the ETO sterilization process can result in plasticization and adhesion of the coating to the balloon via polymer deformation and flow. In a similar way a completely amorphous bioabsorbable polymer may flow when crimped at elevated temperatures on to the delivery balloon.

Aliphatic polyesters are used in pharmaceutical and biomedical applications, including for example surgical sutures and drug delivery systems. Poly(L-lactide) (PLLA) is one of the most widely studied polymer biomaterials, attractive for its biodegradable and biocompatible properties. However, PLLA is not ideally suited for many aspects of drug delivery systems, including those involving drug-eluting stents. Issues of lactide and/or glycolide based drug delivery systems include immiscibility of most drugs with PLLA, compromise of mechanical properties in the fabrication process and deployment of such systems, and lacking control of release of drugs.

The embodiments of the present invention address the above-identified needs and issues.

SUMMARY OF THE INVENTION

In one aspect of the present invention, the present invention provides an implantable article, which comprises an amorphous terpolymer and a semi-crystalline polymer. The amorphous terpolymer comprises lactide, glycolide, and a low $T_g$ monomer. The amorphous terpolymer is admixed with the semi-crystalline polymer or forms a block copolymer with the semi-crystalline polymer.

In some embodiments, optionally with one or any combination of features of the various embodiments above, the semi-crystalline polymer comprises a polyester, e.g., poly(L-lactide).

In some embodiments, optionally with one or any combination of features of the various embodiments above, the amorphous terpolymer has a weight ratio ($R_t$) of about 50% or higher of the total weight of the amorphous terpolymer and the semi-crystalline polymer (R), wherein the semi-crystalline polymer has a weight ratio ($R_s$) of about 50% or below of the total weight of the amorphous terpolymer and the semi-crystalline polymer, and wherein $R_t+R_s=100\%$. In some embodiments, the $R_s$ is from about 10% to about 20%.

In some embodiments, optionally with one or any combination of features of the various embodiments above, the third low $T_g$ monomer is caprolactone, having a molar ratio from about 15% to about 75% or a molar ratio from about 20% to about 40% in the terpolymer.

In some embodiments, optionally with one or any combination of features of the various embodiments above, the amorphous terpolymer is poly(D,L-lactide-glycolide-caprolactone) (PDLLAGACL).

In some embodiments, optionally with one or any combination of features of the various embodiments above, the implantable article is a medical device or a coating on a medical device.

In some embodiments, optionally with one or any combination of features of the various embodiments above, the stent or the coating further comprises a bioactive agent. Examples of the bioactive agent are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, dexamethasone derivatives, glucocorticoids, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, prodrugs thereof, co-drugs thereof, and combinations thereof.

In another aspect of the invention, optionally with one or any combination of features of the various embodiments above, it is provided a method of fabricating an implantable device. The method comprises:

forming an implantable article comprising an amorphous terpolymer and a semi-crystalline polymer, wherein the amorphous terpolymer comprises lactide, glycolide, and caprolactone, wherein the semi-crystalline polymer comprises poly(L-lactide), wherein the amorphous terpolymer is admixed with the semi-crystalline polymer or forms a block copolymer with the semi-crystalline polymer.

In some embodiments, optionally with one or any combination of features of the various embodiments above, the amorphous terpolymer has a weight ratio ($R_t$) of about 50% or higher of the total weight of the amorphous terpolymer and the semi-crystalline polymer (R), wherein the semi-crystalline polymer has a weight ratio ($R_s$) of about 50% or below of the total weight of the amorphous terpolymer and the semi-crystalline polymer, and wherein $R_t+R_s=100\%$. In some embodiments, the $R_s$ is from about 10% to about 20%.

In some embodiments, optionally with one or any combination of features of the various embodiments above, the amorphous terpolymer is poly(D,L-lactide-glycolide-caprolactone) (PDLLAGACL) and caprolactone has a molar ratio from about 15% to about 75% or from about 20% to about 45% in the terpolymer.

In some embodiments, optionally with one or any combination of features of the various embodiments above, the implantable medical device is a stent or a coating on a stent.

In some embodiments, optionally with one or any combination of features of the various embodiments above, the stent or the coating further comprises a bioactive agent. Examples of the bioactive agent are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, dexamethasone derivatives, glucocorticoids, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, prodrugs thereof, co-drugs thereof, and combinations thereof.

In a further aspect of the present invention, optionally with one or any combination of features of the various embodiments above, it is provided a block copolymer comprising an amorphous terpolymer and a semi-crystalline polymer.

In some embodiments, optionally with one or any combination of features of the various embodiments above, the amorphous terpolymer comprises lactide, glycolide, and caprolactone.

In some embodiments, optionally with one or any combination of features of the various embodiments above, the semi-crystalline polymer comprises poly(L-lactide).

In some embodiments, optionally with one or any combination of features of the various embodiments above, the amorphous terpolymer has a weight ratio ($R_t$) of about 50% or higher of the total weight of the amorphous terpolymer and the semi-crystalline polymer (R), wherein the semi-crystalline polymer has a weight ratio ($R_s$) of about 50% or below of the total weight of the amorphous terpolymer and the semi-crystalline polymer, and wherein $R_t+R_s=100\%$. In some embodiments, the $R_s$ is from about 10% to about 20%.

In some embodiments, optionally with one or any combination of features of the various embodiments above, caprolactone has a molar ratio from about 15% to about 75% or from about 20% to about 40% in the terpolymer.

In a still further aspect of the present invention, it is provided a method of treating, preventing, or ameliorating a vascular medical condition, comprising implanting in a patient an implantable medical comprising any of the implantable article described above. The vascular medical condition can be restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

In one aspect of the present invention, the present invention provides an implantable article, which comprises an amorphous terpolymer and a semi-crystalline polymer. The amorphous terpolymer comprises lactide, glycolide, and a low $T_g$ monomer. The amorphous terpolymer is admixed with the semi-crystalline polymer or forms a block copolymer with the semi-crystalline polymer.

In some embodiments, optionally with one or any combination of features of the various embodiments above, the semi-crystalline polymer comprises a polyester, e.g., poly(L-lactide).

In some embodiments, optionally with one or any combination of features of the various embodiments above, the amorphous terpolymer has a weight ratio ($R_t$) of about 50% or higher of the total weight of the amorphous terpolymer and the semi-crystalline polymer (R), wherein the semi-crystalline polymer has a weight ratio ($R_s$) of about 50% or below of the total weight of the amorphous terpolymer and the semi-crystalline polymer, and wherein $R_t+R_s=100\%$. In some embodiments, the $R_s$ is from about 10% to about 20%.

In some embodiments, optionally with one or any combination of features of the various embodiments above, the third low $T_g$ monomer is caprolactone, having a molar ratio from about 15% to about 75% or a molar ratio from about 20% to about 40% in the terpolymer.

In some embodiments, optionally with one or any combination of features of the various embodiments above, the amorphous terpolymer is poly(D,L-lactide-glycolide-caprolactone) (PDLGACL).

In some embodiments, optionally with one or any combination of features of the various embodiments above, the implantable article is a medical device or a coating on a medical device.

In some embodiments, optionally with one or any combination of features of the various embodiments above, the stent or the coating further comprises a bioactive agent. Examples of the bioactive agent are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, dexamethasone derivatives, glucocorticoids, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, prodrugs thereof, co-drugs thereof, and combinations thereof.

In another aspect of the invention, optionally with one or any combination of features of the various embodiments above, it is provided a method of fabricating an implantable device. The method comprises:

forming an implantable article comprising an amorphous terpolymer and a semi-crystalline polymer, wherein the amorphous terpolymer comprises lactide, glycolide, and caprolactone, wherein the semi-crystalline polymer comprises poly(L-lactide), wherein the amorphous terpolymer is admixed with the semi-crystalline polymer or forms a block copolymer with the semi-crystalline polymer.

In some embodiments, optionally with one or any combination of features of the various embodiments above, the amorphous terpolymer has a weight ratio ($R_t$) of about 50% or higher of the total weight of the amorphous terpolymer and the semi-crystalline polymer (R), wherein the semi-crystalline polymer has a weight ratio ($R_s$) of about 50% or below of the total weight of the amorphous terpolymer and the semi-crystalline polymer, and wherein $R_t+R_s=100\%$. In some embodiments, the $R_s$ is from about 10% to about 20%.

In some embodiments, optionally with one or any combination of features of the various embodiments above, the amorphous terpolymer is poly(D,L-lactide-glycolide-caprolactone) (PDLLAGACL) and caprolactone has a molar ratio from about 15% to about 75% or from about 20% to about 45% in the terpolymer.

In some embodiments, optionally with one or any combination of features of the various embodiments above, the implantable medical device is a stent or a coating on a stent.

In some embodiments, optionally with one or any combination of features of the various embodiments above, the stent or the coating further comprises a bioactive agent. Examples of the bioactive agent are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, dexamethasone derivatives, glucocorticoids, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, prodrugs thereof, co-drugs thereof, and combinations thereof.

In a further aspect of the present invention, optionally with one or any combination of features of the various embodiments above, it is provided a block copolymer comprising an amorphous terpolymer and a semi-crystalline polymer.

In some embodiments, optionally with one or any combination of features of the various embodiments above, the amorphous terpolymer comprises lactide, glycolide, and caprolactone.

In some embodiments, optionally with one or any combination of features of the various embodiments above, the semi-crystalline polymer comprises poly(L-lactide).

In some embodiments, optionally with one or any combination of features of the various embodiments above, the amorphous terpolymer has a weight ratio ($R_t$) of about 50% or higher of the total weight of the amorphous terpolymer and the semi-crystalline polymer (R), wherein the semi-crystalline polymer has a weight ratio ($R_s$) of about 50% or below of the total weight of the amorphous terpolymer and the semi-crystalline polymer, and wherein $R_t+R_s=100\%$. In some embodiments, the $R_s$ is from about 10% to about 20%.

In some embodiments, optionally with one or any combination of features of the various embodiments above, caprolactone has a molar ratio from about 15% to about 75% or from about 20% to about 40% in the terpolymer.

In a still further aspect of the present invention, it is provided a method of treating, preventing, or ameliorating a vascular medical condition, comprising implanting in a patient an implantable medical comprising any of the implantable article described above. The vascular medical condition can be restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

Generally, an implantable article described herein can degrade or absorb at a rate that the coating will have about 80% or more mass loss within a period of 6 months after deployment (e.g., implanted in a blood vessel of a patient). In some embodiments, the coating mass loss within the same period can be about 90% or more, 95% or more, or about 99% or more.

In some embodiments, the term "domain" can be referred to as "phase." Therefore, the term "crystalline domain" can be referred to as "crystalline phase." Similarly, the term "amorphous domain" can be referred to as "amorphous phase."

As used herein, the term "semi-crystalline copolymer" is used interchangeably with the term "semi-crystalline polymer." In some embodiments, the semi-crystalline polymer can be a copolymer formed of two or more monomers. In some embodiments, the semi-crystalline polymer can be a homopolymer formed of one monomer.

The implantable article described herein is generally degradable or bioabsorbable. In some embodiments, the coating can degrade within about 1 month, 2 months, 3 months, 4 months, 6 months, 12 months, 18 months, or 24 months after implantation of a medical device comprising the coating. In some embodiments, the coating can completely degrade or absorb within 24 months after implantation of a medical device comprising the coating.

In some embodiments, the implantable article (e.g., an implantable medical device or a coating on an implantable medical device such as stent) can include one or more other biocompatible polymers, which are described below.

The implantable article described herein can be formed on an implantable device such as a stent, which can be implanted in a patient to treat, prevent, mitigate, or reduce a vascular medical condition, or to provide a pro-healing effect. In some embodiments, the vascular medical condition or vascular condition is a coronary artery disease (CAD) and/or a peripheral vascular disease (PVD). Some examples of such vascular medical diseases are restenosis and/or atherosclerosis. Some other examples of these conditions include thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DEFINITIONS

Wherever applicable, the definitions to some terms used throughout the description of the present invention as provided below shall apply.

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 kDa) or less. The process of breaking down and eventual absorption and elimination of the polymer or coating can be caused by, e.g., hydrolysis, metabolic processes, oxidation, enzymatic processes, bulk or surface erosion, and the like. Conversely, a "biostable" polymer or coating refers to a polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal."

In the context of a blood-contacting implantable device, a "prohealing" drug or agent refers to a drug or agent that has the property that it promotes or enhances re-endothelialization of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.*, 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.*, 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs*, 29: 455-473 (1985).

The terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device. As used herein, an "implantable device" may be any suitable substrate that can be implanted in a human or non-human animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages. An implantable device can be designed for the localized delivery of a therapeutic agent. A medicated implantable device may be constructed in part, e.g., by coating the device with a coating material containing a therapeutic agent. The body of the device may also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a material that is described as a layer or a film (e.g., a coating) "disposed over" an indicated substrate (e.g., an implantable device) refers to, e.g., a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate. In some embodiments, the term a "layer" or a "film" excludes a film or a layer formed on a non-implantable device.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

Amorphous Terpolymers

The amorphous terpolymers described herein can have different contents of the lactide (A), glycolide (B), and a third, low $T_g$ monomer (C). The terpolymer can be expressed in this general formula $A_xB_yC_z$, wherein x, y and z are ratios of A, B, and C, respectively. Within the terpolymer, monomers A, B, and C can have any sequence of arrangement, for example, ABC, BAC, CBA, ACB, ABAC, ABBC, BABC, BAAC, BACC, CBCA, CBBA, CBAA, ABACA, ABACB, ABACC, AABAC, BABCA, BABCB, BABCC, etc. As outlined in some embodiments, a sequence of monomers or units can have more than one units of a monomer, which are described in more detail below.

Terpolymers with different contents of these three monomers have different properties with regard to, e.g., rate of degradation, mechanical properties, drug permeability, water permeability, and drug release rate, depending on a particular composition of the monomers in the terpolymer.

In some embodiments, the terpolymer can have a $T_g$ below about 37° C. This terpolymer can have units derived from D-lactide, L-lactide, or D,L-lactide from about 10% to about 80% by weight. Monomers such as D-lactide, L-lactide, glycolide, and dioxanone can crystallize if present in high concentration in a polymer. However, crystallization of units from any of these monomers can be minimized or prevented if concentration of each is below 80% by weight and randomly distributed in the polymer. Therefore, the composition of a terpolymer described herein shall include units of D-lactide or L-lactide at about 10-80% by weight, units of glycolide at about 5-80% by weight and units from the third, low $T_g$ monomer at about 5-60% by weight. The terpolymer can have a weight-average molecular weight ($M_w$) of about 10K Daltons or above, preferably from about 20K Daltons to about 600K Daltons.

Ratios of units from the lactide, glycolide and the low $T_g$ monomers can vary, forming a terpolymer having different properties, e.g., different degradation rates, different rates of release of a drug from a coating formed of the terpolymer, different drug permeability, different flexibility or mechanical properties. As noted above, generally, the glycolide provides an accelerated or enhanced degradation of the terpolymer, the lactide monomer provides mechanical strength to the terpolymer, and the third, low $T_g$ monomer can enhance drug permeability, water permeability, and enhancing degradation rate of the polymer, imparting greater flexibility and elongation, and improving mechanical properties of a coating formed of the terpolymer.

In some embodiments, the ratio of the various monomers can vary along the chain of the terpolymer. In such a terpolymer, one point of the chain of polymer can be heavy with one monomer while another point of the chain can be light with the same monomer, for example. If a monofunctional initiator is used, and if the selected monomers have highly different reactivity ratios, then a gradient of composition is generated as the monomers are consumed during the polymerization. In another methodology, such a terpolymer can be prepared by so-called gradient polymerization wherein during the polymerization a first or second monomer is progressively added to the reactor containing all, or a portion of, the first monomer. (Matyjaszewski K. and Davis T. P. eds. Handbook of Radical Polymerization, John Wiley & Sons, 2002, p. 789). Yet a third method is by introducing blocks of various ratios of the monomers into the chain of the terpolymer.

In some embodiments, the terpolymer described herein can be used to build one or more blocks in combination with other blocks such as poly(ethylene glycol) (PEG) or other blocks of biodegradable or biodurable polymers described below.

Randomness of the terpolymer described herein can be measured by randomness index. Generally, a perfectly alternating co-polymer would have a degree of randomness of 1. Conversely, in some embodiments, the terpolymer can include all the repeating units of the monomers in three blocks, the lactide block, the glycolide block, and the block of the third, low $T_g$ monomer. Such a terpolymer would have a degree of randomness of 0. These are known as block copolymers. In some other embodiments, the terpolymer can have a degree of randomness ranging from above 0 to below 1, for example, about 0.01, about 0.02, about 0.05, about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, or about 0.99. Generally, for a crystalline domain to develop, one usually needs a pentad (i.e. the same 5 repeat units or monomers in sequence). Therefore, in some embodiments, one factor to control the randomness of the terpolymer is to keep the repeat units or monomers in sequence in the terpolymer below 5, e.g., 1, 2, 3, or 4.

Randomness in a polymer can be readily determined by established techniques in the art. One such technique is NMR analysis ((see, e.g., J. Kasperczyk, Polymer, 37(2): 201-203 (1996); Mangkorn Srisa-ard, et al., Polym Int., 50:891-896 (2001)).

Randomness of an amorphous terpolymer can be readily controlled or varied using techniques known in the art. For example, randomness in a batch reactor is controlled by polymerization temperature and type of solvent where the monomer reactivity ratios will change. For continuous reactors, it will also depend on monomer feed ratios and temperature. Secondarily, there is also a pressure effect on reactivity ratios. Monomers relative reactivity is also important, so you can control it by selecting monomers with similar or different reactivity.

As mentioned previously, in some embodiments, one requisite attribute of the third monomer is that, if a homopolymer were to be formed of the third monomer, the homopolymer would have a $T_g$ below about −20° C. The third monomer can be any monomer that is capable of forming a terpolymer with lactide and glycolide. In some embodiments, the third low $T_g$ monomer is a lactone, a carbonate, a thiocarbonate, an oxaketocycloalkane, or a thiooxaketocyclolakane. In some embodiments, the lactone, carbonate, thiocarbonate, oxaketocycloalkane, or thiooxaketocyclolakane can have hydrocarbyl or alkoxy substituent(s). In some embodiments, the substituent(s) can include hetero atom(s) such as a halo (F, Cl, Br or I) group(s). Some examples of substituents include, but are not limited to, methoxy, ethoxy, or a C1-C12 hydrocarbon group.

Some examples of the third monomer are given below in Table 1.

TABLE 1

Examples of low $T_g$ monomers

1. 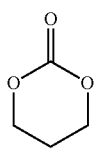

trimethylene
carbonate
$T_g = -15°$ C.

2. 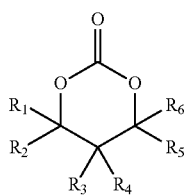

substituted trimethylele-
carbonate
$R_1$—$R_6$ are independently H,
$CH_3O$, $C_1$—$C_{12}$ hydrocarbon 3. 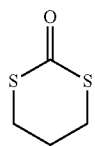

trimethylene
dithiocarbonate

4. 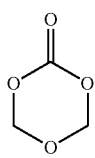

1,3,5-trioxa-4-
ketocyclohexane

5. 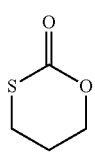

trimethylene
thiocarbonate

6. 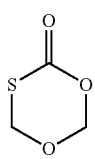

1-thio-3,5-dioxa-2-
ketocyclohexane

TABLE 1-continued

Examples of low $T_g$ monomers

7. 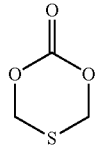

1-thio-3,5-dioxa-4-
ketocyclohexane

8. 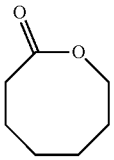

ξ-enantholactone

9. 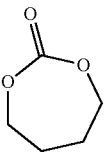

tetramethylene
carbonate

10. 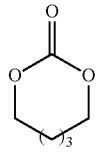

pentamethylene
carbonate

11. 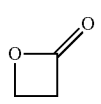

β-butyrolactone

12. 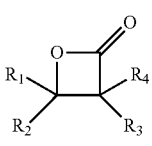

substituted β-
butyrolactone
R1—R4 are independently H,
$CH_3O$, $C_1$—$C_{12}$ hydrocarbon 13. 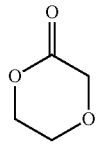

dioxanone

TABLE 1-continued

Examples of low $T_g$ monomers

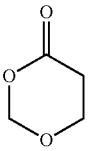

14. 1,3-dioxa-cyclo-hexyl-6-one

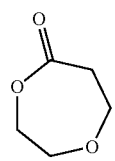

15. 1,4-dioxa-7-keto-cycloheptane or 1,4- dioxa-cycloheptyl-7-one

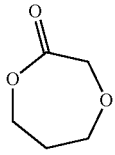

16. 1,4-dioxa-2-keto-cycloheptane or 1,4-dioxa-cycloheptyl-2-one

Semi-Crystalline Polymers

The semi-crystalline polymers described herein can have crystalline domains and amorphous domains. The semi-crystalline polymer must have one or more crystalline domains having one or more crystalline polymer structures with a molar ratio sum of the crystalline domains (x, e.g., 10-30% crystallinity) (having $T_m$s) and one or more amorphous domains having one or more amorphous polymer structures with a molar ratio sum of the amorphous domains (y) (having glass transition temperatures, $T_g$) that meet the definition set forth by the following equation:

$$x+y=1 \qquad \text{(equation 1);}$$

In some embodiments, the semi-crystalline polymer has a crystalline domain having a $T_m$ of about 60° C. or above. In these embodiments, the glass transition temperature of the amorphous domain can be lower than $T_t$.

In equation 1, x and y can each range from about 0.01 to about 0.99. Some exemplary values for x and y, independently, are, about 0.02, about 0.05, about 0.1, about 0.2, about 0.3, about 0.4, about 0.5, about 0.6, about 0.7, about 0.8, about 0.9, about 0.95, or about 0.98.

The term "$T_t$" can be the temperature of working process of any coating procedure or a treatment process at any given time point. For example, $T_t$ can be the temperature of a baking procedure, a crimping procedure, or an ETO sterilization procedure. Therefore, $T_t$ can be a temperature above the ambient temperature (e.g., above 25° C.) but below about 150° C. In some embodiments, $T_t$ can be about 50° C., about 80° C., about 100° C., or about 120° C.

In some embodiments, the semi-crystalline copolymer can be, e.g., poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(D-lactic acid-co-glycolide-co-caprolactone) (PDLA-GA-CL), poly(L-lactic acid-co-glycolide-co-caprolactone) (PLLA-GA-CL), poly(DL-lactic acid-co-glycolide-co-caprolactone) (PDLLA-GA-CL), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL) or any other semi-crystalline co-polymers made out of aliphatic polyesters. In all the polymers comprising both D-lactide and L-lactide the ratio of the two diastereomers could vary from 0-100, being for example 0.10, 0.50, 1, 5, 10, 20, 30, 40, 50, 60, 70, 80, 90, 95, 99, 99.5, 99.9 or any other ratio. It is assumed the when L-lactic acid or glycolic acid is used in naming a copolymer this is also equivalent to L-lactide and glycolide. In any of the previously mentioned polymers the D- or the L-lactide could alternatively be replaced with meso-lactide.

These semi-crystalline polymer blocks have a molar ratio of the crystalline domains, x, and a molar ratio of the amorphous domains, y, as defined above, and can be random in structure or have a more block structure, or have the design of a true block copolymer. The block copolymer could be di-block, tri-block, tetra-block or penta-block co-polymers.

In some embodiments, the semi-crystalline copolymer can be a semi-crystalline terpolymer. Such terpolymer includes repeating units from three different monomers and can include one monomer or two different monomers for providing a crystalline domain and one monomer or two different monomers for providing an amorphous domain. While the specific ratio(s) of the monomers may vary, the terpolymer will have repeating units from three different monomers, and the terpolymer will have a molar ratio, x, of the crystalline domain, which can include repeating units from one or two different monomers, and a molar ratio, y, of the amorphous domain in the terpolymer, which can include repeating units from one monomer or two different monomers, as defined above. In some embodiments, the one monomer or two different monomers providing a crystalline domain to the terpolymer can be, e.g., L-lactic acid, D-lactic acid, glycolic acid, caprolactone, dioxanone. The one monomer or two different monomers providing an amorphous domain to the terpolymer can be, e.g., caprolactone, substituted caprolactone, glycolic acid, D,L-lactic acid, L-lactic acid, D-Lactic acid, meso-lactic acid, trimethylene carbonate, or substituted trimethylene carbonate.

In some embodiments, the semi-crystalline polymer can be a semi-crystalline block copolymer. Such copolymer includes repeating units one or more monomers for providing the crystalline domains (crystalline block) and one or more monomers for providing the amorphous domains (amorphous block). Where the crystalline blocks would also provide amorphous domains and further the crystalline domain or block and/or the amorphous domain or block include repeating units from one or more different monomers, such the monomers forming the crystalline domain or block, e.g., monomers A, B, C . . . , can have different molar ratio(s), independently ranging from 0 to about 100, for example, and such monomers forming the amorphous domain or block, e.g., monomers A', B', C' . . . , can have different molar ratio(s), independently ranging from 0 to about 100, for example. However, the semi-crystalline polymer copolymer must have a molar ratio, x, of the crystalline domain or block and a molar ratio, y, of the amorphous domain or block as defined above. In some embodiments, the monomer(s) providing a crystalline domain to the semi-crystalline polymer copolymer can be, e.g., L-lactic acid, D-lactic acid, glycolic acid, caprolactone, dioxanone. The monomer(s) providing an amorphous domain to the semi-crystalline polymer copolymer can be, e.g., caprolactone, substituted caprolactone, glycolic acid, D,L-lactic acid, L-lactic acid, D-Lactic acid, meso-lactic acid, trimethylene carbonate, or substituted trimethylene carbonate, poly(ethylene glycol) (PEG), poly(propylene oxide) (PPO), amides, or any other bioabsorable segment.

In some embodiments, the semi-crystalline polymer can be a semi-crystalline poly(ester amide) (PEA). Such a PEA polymer can include a crystalline domain and an amorphous domain. The crystalline domain and the amorphous domain each have a molar ratio, x and y, as defined above. Some examples of semi-crystalline PEA polymers include, but are not limited to, those comprising L-phenyl alanine, D-phenyl alanine, or other units that would make a polymer crystallize such as long aliphatic chains or aromatic groups.

In some further embodiments, the semi-crystalline polymer can be any of the following polymers:

semi-crystalline PLLGA with content of L-lactide ranging from about 65 molar % to about 100 molar %;

semi-crystalline PLLA-GA-CL terpolymer with content of L-lactide ranging from about 65 molar % or higher; and semi-crystalline PLLA-CL (L-lactide/CL=75/25 or 70/30 by molar).

The molecular weights of the above polymers can vary. In some embodiments, the weight average molecular weight (Mw) of these polymers can range from about 75K Daltons to about 250K Daltons. In some embodiments, the Mw of these polymers range from about 100K Daltons to about 200K Daltons.

In some embodiments, the term "crystalline domain(s)" or "amorphous domain(s)" can be referred to as "crystalline unit(s)" or "amorphous unit(s)." In some embodiments, the term "repeating unit(s)" can also be referred to as "crystalline unit(s)" or "amorphous unit(s)."

Biologically Active Agents

In some embodiments, the implantable device described herein can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), deforolimus, temsirolimus, prodrugs thereof, co-drugs thereof, and combinations thereof. An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.*, 70A:10-19 (2004). Endothelial cells can be selectively targeted (for the targeted delivery of immunoliposomes) using scFv A5. T. Volkel, et al., *Biochimica et Biophysica Acta*, 1663:158-166 (2004). Junction membrane protein vascular endothelial (VE)-cadherin has been shown to bind to endothelial cells and down regulate apoptosis of the endothelial cells. R. Spagnuolo, et al., *Blood*, 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy) ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), temsirolimus, deforolimus, pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is clobetasol.

An alternative class of drugs would be p-para-α-agonists for increased lipid transportation, examples include fenofibrate.

In some embodiments, optionally in combination with one or more other embodiments described herein, the at least one biologically active agent specifically cannot be one or more of any of the bioactive drugs or agents described herein.

Coating Construct

According to some embodiments of the invention, optionally in combination with one or more other embodiments described herein, a coating disposed over an implantable device (e.g., a stent) can include an invention polymer mixture or block copolymer in the reservoir layer and an amorphous polymer in the primer layer described herein in a layer according to any design of a coating. The coating can be a multi-layer structure that includes at least one primer layer, which is layer (1) described below, and at least one reservoir layer, which is layer (2) described below, and can include any of the following (3), (4) and (5) layers or combination thereof:

(1) a primer layer;
(2) a reservoir layer (also referred to "matrix layer" or "drug matrix"), which can be a drug-polymer layer including at least one polymer (drug-polymer layer) or, alternatively, a polymer-free drug layer;
(3) a release control layer (also referred to as a "rate-limiting layer");
(4) a topcoat layer; and/or
(5) a finishing coat layer.

In some embodiments, a coating of the invention can include two or more reservoir layers described above, each of which can include a bioactive agent described herein.

Each layer of a coating can be disposed over the implantable device (e.g., a stent) by dissolving the invention polymer mixture or block copolymer, optionally with one or more other polymers, in a solvent, or a mixture of solvents, and disposing the resulting coating solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C. for a period of time between about 5 minutes and about 60 minutes, if desired, to allow for crystallization of the polymer coating, and/or to improve the thermodynamic stability of the coating.

To incorporate a bioactive agent (e.g., a drug) into the reservoir layer, the drug can be combined with the polymer solution that is disposed over the implantable device as described above. Alternatively, if it is desirable a polymer-free reservoir can be made. To fabricate a polymer-free reservoir, the drug can be dissolved in a suitable solvent or mixture of solvents, and the resulting drug solution can be disposed over the implantable device (e.g., stent) by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied indirectly over at least a portion of the stent surface to serve as a reservoir for at least one bioactive agent (e.g., drug) that is incorporated into the reservoir layer over at least a portion of the primer layer. The primer layer can be applied between the stent and the reservoir to improve the adhesion of the drug-polymer layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

Sterilization of a coated medical device generally involves a process for inactivation of micropathogens. Such processes are well known in the art. A few examples are e-beam, ETO sterilization, autoclaving, and gamma irradiation. Most, if not all, of these processes can involve an elevated temperature. For example, ETO sterilization of a coated stent generally involves heating above 50° C. at humidity levels reaching up to 100% for periods of a few hours up to 24 hours. A typical EtO cycle would have the temperature in the enclosed chamber to reach as high as above 50° C. within the first 3-4 hours then and fluctuate between 40° C. to 50° C. for 17-18 hours while the humidity would reach the peak at 100% and maintain above 80% during the fluctuation time of the cycle.

The process of the release of a drug from a coating having both topcoat and finishing coat layers includes at least three steps. First, the drug is absorbed by the polymer of the topcoat layer at the drug-polymer layer/topcoat layer interface. Next, the drug diffuses through the topcoat layer using the void volume between the macromolecules of the topcoat layer polymer as pathways for migration. Next, the drug arrives at the topcoat layer/finishing layer interface. Finally, the drug diffuses through the finishing coat layer in a similar fashion, arrives at the outer surface of the finishing coat layer, and desorbs from the outer surface. At this point, the drug is released into the blood vessel or surrounding tissue. Consequently, a combination of the topcoat and finishing coat layers, if used, can serve as a rate-limiting barrier. The drug can be released by virtue of the degradation, dissolution, and/or erosion of the layer(s) forming the coating, or via migration of the drug through the invention polymer mixture or block copolymeric layer(s) into a blood vessel or tissue.

In one embodiment, except for the primer layer, any or all of other layers of the stent coating can be made of an invention polymer mixture or block copolymer described herein, optionally having the properties of being biologically degradable/erodable/absorbable/resorbable, non-degradable/biostable polymer, or a combination thereof.

In another embodiment, except for the reservoir layer, any or all of other layers of the stent coating can be made of an amorphous polymer described herein, optionally having the properties of being biologically degradable/erodable/absorbable/resorbable, non-degradable/biostable polymer, or a combination thereof.

If a finishing coat layer is not used, the topcoat layer can be the outermost layer and can be made of an invention polymer mixture or block copolymer described herein and optionally having the properties of being biodegradable or, biostable, or being mixed with an amorphous polymer. In this case, the remaining layers (i.e., the primer and the reservoir layer) optionally can also be fabricated of an invention polymer mixture or block copolymer described herein and optionally having the properties of being biodegradable or, biostable, or being mixed with an amorphous polymer The polymer(s) in a particular layer may be the same as or different than those in any of the other layers, as long as the outside of another bioabsorbable should preferably also be bioabsorbable and degrade at a similar or faster relative to the inner layer.

If neither a finishing coat layer nor a topcoat layer is used, the stent coating could have only two layers—the primer and the reservoir. In such a case, the reservoir is the outermost layer of the stent coating and should be made of an invention polymer mixture or block copolymer described herein and optionally having the properties of being biodegradable or, biostable, or being mixed with an amorphous polymer. The primer layer is fabricated of an amorphous polymer described herein and optionally one or more biodegradable polymer(s), biostable polymer(s), or a combination thereof.

Any layer of a coating, except for the primer layer, can contain any amount of an invention polymer mixture or block copolymer described herein and optionally having the properties of being biodegradable or, biostable. Non-limiting examples of bioabsorbable polymers and biocompatible polymers include poly(N-vinyl pyrrolidone); polydioxanone; polyorthoesters; polyanhydrides; poly(glycolic acid); poly(glycolic acid-co-trimethylene carbonate); polyphosphoesters; polyphosphoester urethanes; poly(amino acids); poly(trimethylene carbonate); poly(iminocarbonates); co-poly(ether-esters); polyalkylene oxalates; polyphosphazenes; biomolecules, e.g., fibrin, fibrinogen, cellulose, cellophane, starch, collagen, hyaluronic acid, and derivatives thereof (e.g., cellulose acetate, cellulose butyrate, cellulose acetate butyrate, cellulose nitrate, cellulose propionate, cellulose ethers, and carboxymethyl cellulose), polyurethane, polyesters, polycarbonates, polyurethanes, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), or any copolymers thereof.

Any layer of a stent coating can also contain any amount of a non-degradable polymer, or a blend of more than one such polymer as long as it is not mixed with a bioabsorbable polymer or any layer underneath the non-degradable layer comprise a bioabsorbable polymer. Non-limiting examples of non-degradable polymers include poly(methylmethacrylate), poly(ethylmethacrylate), poly(butylmethacrylate), poly(2-ethylhexylmethacrylate), poly(laurylmethacrylate), poly(2-hydroxyethyl methacrylate), polyethylene glycol (PEG) acrylate, PEG methacrylate, 2-methacryloyloxyethylphosphorylcholine (MPC) and poly(n-vinyl pyrrolidone), poly(methacrylic acid), poly(acrylic acid), poly(hydroxypropyl methacrylate), poly(hydroxypropylmethacrylamide), poly(3-trimethylsilylpropyl methacrylate), and copolymers thereof.

Method of Fabricating Implantable Device

Other embodiments of the invention, optionally in combination with one or more other embodiments described herein, are drawn to a method of fabricating an implantable device. In one embodiment, the method comprises forming the implantable device of a material containing a biodegradable or biostable polymer or copolymer.

Under the method, a portion of the implantable device or the whole device itself can be formed of the material containing a biodegradable or biostable polymer or copolymer. The method can deposit a coating having a range of thickness over an implantable device. In certain embodiments, the method deposits over at least a portion of the implantable device a coating that has a thickness of ≤about 30 microns, or ≤about 20 microns, or ≤about 10 microns, or ≤about 5 microns.

In certain embodiments, the method is used to fabricate an implantable device selected from stents, grafts, stent-grafts, catheters, leads and electrodes, clips, shunts, closure devices, valves, and particles. In a specific embodiment, the method is used to fabricate a stent.

In some embodiments, to form an implantable device formed from a polymer, a polymer or copolymer optionally including at least one bioactive agent described herein can be formed into a polymer construct, such as a tube or sheet that can be rolled or bonded to form a construct such as a tube. An implantable device can then be fabricated from the construct. For example, a stent can be fabricated from a tube by laser machining a pattern into the tube. In another embodiment, a polymer construct can be formed from the polymeric material of the invention using an injection-molding apparatus.

Non-limiting examples of polymers, which may or may not be the invention polymer mixture or block copolymers defined above, that can be used to fabricate an implantable device include poly(N-acetylglucosamine) (Chitin), Chitosan, poly(hydroxyvalerate), poly(lactide-co-glycolide), poly (hydroxybutyrate), poly(hydroxybutyrate-co-valerate), polyorthoester, polyanhydride, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly (DL-lactic acid-glycolic acid (PDLLA-GA), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), poly(thioesters), poly(trimethylene carbonate), polyethylene amide, polyethylene acrylate, poly(glycolic acid-co-trimethylene carbonate), co-poly(ether-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides (e.g., polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, rayon-triacetate, cellulose and derivates thereof (e.g., cellulose acetate, cellulose butyrate, cellulose acetate butyrate, cellophane, cellulose nitrate, cellulose propionate, cellulose ethers, and carboxymethyl cellulose), and copolymers thereof.

Additional representative examples of polymers that may be suited for fabricating an implantable device include ethylene vinyl alcohol copolymer (commonly known by the generic name EVOH or by the trade name EVAL), poly (butyl methacrylate), poly(vinylidene fluoride-co-hexafluoropropylene) (e.g., SOLEF 21508, available from Solvay Solexis PVDF of Thorofare, N.J.), polyvinylidene fluoride (otherwise known as KYNAR, available from ATOFINA Chemicals of Philadelphia, Pa.), poly(tetrafluoroethylene-co-hexafluoropropylene-co-vinylidene fluoride), ethylene-vinyl acetate copolymers, and polyethylene glycol.

Method of Treating or Preventing Disorders

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. A portion of the implantable device or the whole device itself can be formed of the material, as described herein. For example, the material can be a coating disposed over at least a portion of the device.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a particular embodiment, the condition or disorder is atherosclerosis, thrombosis, restenosis or vulnerable plaque.

In one embodiment of the method, optionally in combination with one or more other embodiments described herein, the implantable device is formed of a material or includes a coating containing at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), temsirolimus, deforolimus, pimecrolimus, imatinib mesylate, midostaurin, clobetasol, progenitor cell-capturing antibodies, prohealing drugs, fenofibrate, prodrugs thereof, co-drugs thereof, and a combination thereof.

In certain embodiments, optionally in combination with one or more other embodiments described herein, the implantable device used in the method is selected from stents, grafts, stent-grafts, catheters, leads and electrodes, clips, shunts, closure devices, valves, and particles. In a specific embodiment, the implantable device is a stent.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

The invention claimed is:

1. An implantable article, comprising an amorphous terpolymer and a semi-crystalline polymer, wherein the amorphous terpolymer is admixed with the semi-crystalline polymer;
   wherein the amorphous terpolymer comprises lactide, glycolide, and a low $T_g$ monomer; wherein the low $T_g$ monomer is selected from the group consisting of trimethylene carbonate, trimethylene dithiocarbonate, 1,3,5-trioxa-4-ketocyclohexane, trimethylene thiocarbonate, 1-thio-3,5-dioxa-2-ketocyclohexane, 1-thio-3, 5-dioxa-4-keto-cyclohexane, 8-ξ-enantholactone, tetramethylene carbonate, pentamethylene carbonate, β-butyrolactone, dioxanone, 1,3-dioxa-cyclohexyl-6-one, 1,4-dioxa-7-ketocycloheptane, 1,4-dioxacycloheptyl-7-one, 1,4-dioxa-2-keto-cycloheptane, and 1,4-dioxacycloheptyl-2-one;
   wherein the semi-crystalline polymer is a semi-crystalline poly(ester amide) (PEA) or a semi-crystalline copolymer selected from poly(L-lactic acid-co-caprolactone) (PLLA-CL), poly(D-lactic acid-co-caprolactone) (PDLA-CL), poly(DL-lactic acid-co-caprolactone) (PDLLA-CL), and poly(glycolide-co-caprolactone) (PGA-CL).

2. The implantable article of claim 1, wherein the semi-crystalline polymer comprises poly(L-lactide).

3. The implantable article of claim 1, wherein the semi-crystalline polymer is a semi-crystalline PLLA-CL with ratio of L-lactide and caprolactone being 75/25 or 70/30.

4. The implantable article of claim 1, wherein the amorphous terpolymer has a weight ratio ($R_t$) of about 50% or higher of the total weight of the amorphous terpolymer and the semi-crystalline polymer (R), wherein the semi-crystalline polymer has a weight ratio ($R_s$) of about 50% or below of the total weight of the amorphous terpolymer and the semi-crystalline polymer, and wherein $R_t+R_s=100\%$.

5. The implantable article of claim 4, wherein the $R_s$ is from about 10% to about 20%.

6. The implantable article of claim 1, which is a medical device or a coating on a medical device.

7. The implantable article of claim 1, which is a stent or a coating on a stent.

8. The implantable article of claim 7, wherein the stent or the coating further comprises a bioactive agent.

9. The implantable article of claim 8, wherein the bioactive agent is selected from paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, dexamethasone derivatives, glucocorticoids, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, prodrugs thereof, co-drugs thereof, and combinations thereof.

10. The implantable article of claim 1, wherein the semi-crystalline PEA comprises L-phenyl alanine or D-phenyl alanine.

11. The implantable article of claim 1, wherein the semi-crystalline polymer is a block copolymer comprising a crystalline block and an amorphous block.

12. A method of fabricating an implantable device, comprising
forming an implantable article comprising an amorphous terpolymer and a semi-crystalline polymer,
wherein the amorphous terpolymer comprises lactide, glycolide, and a low $T_g$ monomer; wherein the low T. monomer is selected from the group consisting of trimethylene carbonate, trimethylene dithiocarbonate, 1,3,5-trioxa-4-ketocyclohexane, trimethylene thiocarbonate, 1-thio-3,5-dioxa-2-ketocyclohexane, 1-thio-3,5-dioxa-4-keto-cyclohexane, 8-ξ-enantholactone, tetramethylene carbonate, pentamethylene carbonate, β-butyrolactone, dioxanone, 1,3-dioxa-cyclohexyl-6-one, 1,4-dioxa-7-ketocycloheptane, 1,4-dioxacycloheptyl-7-one, 1,4-dioxa-2-keto-cycloheptane, and 1,4-dioxacycloheptyl-2-one;
wherein the semi-crystalline polymer is a semi-crystalline poly(ester amide) (PEA) or a semi-crystalline copolymer selected from poly(L-lactic acid-co-caprolactone) (PLLA-CL), poly(D-lactic acid-co-caprolactone) (PDLA-CL), poly(DL-lactic acid-co-caprolactone) (PDLLA-CL), and poly(glycolide-co-caprolactone) (PGA-CL);
wherein the amorphous terpolymer is admixed with the semi-crystalline polymer.

13. The method of claim 12, wherein the amorphous terpolymer has a weight ratio ($R_t$) of about 50% or higher of the total weight of the amorphous terpolymer and the semi-crystalline polymer (R), wherein the semi-crystalline polymer has a weight ratio ($R_s$) of about 50% or below of the total weight of the amorphous terpolymer and the semi-crystalline polymer, and wherein $R_t+R_s=100\%$.

14. The method of claim 13, wherein the $R_s$ is from about 10% to about 20%.

15. The method of claim 12, wherein the implantable device is a stent or a coating on a stent.

16. The method of claim 15, wherein the stent or the coating further comprises a bioactive agent.

17. The method of claim 16, wherein the bioactive agent is selected from paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, dexamethasone derivatives, glucocorticoids, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, prodrugs thereof, co-drugs thereof, and combinations thereof.

18. A method of treating, preventing, or ameliorating a vascular medical condition, comprising implanting in a patient an implantable medical comprising the implantable article according to claim 9, wherein the vascular medical condition is selected from restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

* * * * *